United States Patent
Biegun et al.

(10) Patent No.: US 8,679,127 B2
(45) Date of Patent: Mar. 25, 2014

(54) ACCESSORIES FOR REMOVING BONE MATERIAL AND METHOD FOR MAKING SAME

(75) Inventors: Jean-François Biegun, Besancon (FR); Pascal Marceaux, Chaumont (FR)

(73) Assignee: Jean-Francois Biegun, Bavilliers (FR)

(*) Notice: Subject to any disclaimer, the term of this patent is extended or adjusted under 35 U.S.C. 154(b) by 405 days.

(21) Appl. No.: 10/534,567

(22) PCT Filed: Nov. 14, 2003

(86) PCT No.: PCT/FR03/03374
§ 371 (c)(1),
(2), (4) Date: May 12, 2005

(87) PCT Pub. No.: WO2004/047655
PCT Pub. Date: Jun. 10, 2004

(65) Prior Publication Data
US 2006/0111725 A1     May 25, 2006

(30) Foreign Application Priority Data
Nov. 22, 2002  (FR) ..................................... 02 14638

(51) Int. Cl.
*A61B 17/00*      (2006.01)
(52) U.S. Cl.
USPC .............................................. 606/87; 606/79

(58) Field of Classification Search
USPC ....................................................... 606/85, 87
See application file for complete search history.

(56) References Cited

U.S. PATENT DOCUMENTS

| | | | | | |
|---|---|---|---|---|---|
| 1,396,934 | A | * | 11/1921 | Judd | 4/237 |
| 4,074,431 | A | | 2/1978 | Beaver et al. | 30/353 |
| 5,124,106 | A | * | 6/1992 | Morr et al. | 264/221 |
| 5,147,408 | A | * | 9/1992 | Noble et al. | 623/23.15 |
| 5,454,815 | A | * | 10/1995 | Geisser et al. | 606/85 |
| 5,490,854 | A | * | 2/1996 | Fisher et al. | 606/88 |
| 5,817,097 | A | * | 10/1998 | Howard et al. | 606/87 |
| 5,897,559 | A | * | 4/1999 | Masini | 606/86 |
| 5,910,106 | A | * | 6/1999 | Morgan et al. | 600/169 |
| 5,916,220 | A | * | 6/1999 | Masini | 606/88 |
| 6,110,177 | A | | 8/2000 | Ebner et al. | 606/84 |
| 6,120,508 | A | * | 9/2000 | Grunig et al. | 606/85 |
| 6,283,971 | B1 | * | 9/2001 | Temeles | 606/81 |
| 6,764,490 | B1 | * | 7/2004 | Szabo | 606/81 |
| 2003/0119935 | A1 | * | 6/2003 | Merrill et al. | 522/150 |

FOREIGN PATENT DOCUMENTS

EP      574701 A1 * 12/1993

* cited by examiner

*Primary Examiner* — Nicholas Woodall
(74) *Attorney, Agent, or Firm* — Renner, Kenner, Greive, Bobak, Taylor & Weber

(57) ABSTRACT

An accessory for removing material for prostheses surgery including a plastic part and an insert made of a material harder than the bone material, the insert being embedded in the plastic part such that if the device is brought to a selected temperature, the accessory deteriorates itself.

10 Claims, 6 Drawing Sheets

ACCESSORIES FOR REMOVING BONE MATERIAL AND METHOD FOR MAKING SAME

This invention relates to instruments or ancillaries used to remove bones for hip or knee prosthetic surgery and in particular to a rasp for fitting a hip prosthesis and to a cutting unit for fitting a knee prosthesis. This invention also relates to a surgeon's ancillary kit, notably for fitting a hip prosthesis comprising a rasp according to the invention and/or for fitting a knee prosthesis comprising a cutting unit according to the invention.

Rasps, cutting units and other ancillaries for removing bones are well-known in the field. These ancillaries must be hard enough and sufficiently resistant to wear to be able to attack bone and withstand the heavy pressures resulting from the action of a blade with which they cooperate on bone. To date, metals have always been used, which are sufficiently resistant to wear to attack the bone. What is more, they can be reused after re-sterilisation in the autoclave.

However, these ancillaries are expensive to produce due to the material used and the manufacturing method (machining). In addition, for reasons of patient safety, it is not desirable for a rasp or a cutting unit of this kind to be reused a second time by a surgeon after he has himself carried out further sterilisation, particularly because of the risk associated with infections such as Kreuzfeld Jakob disease.

The aim of the invention is to overcome these disadvantages by offering an ancillary for removing bone, for surgery to fit a prosthesis, notably a rasp for fitting a hip prosthesis and/or a cutting unit for fitting a knee prosthesis, which may be simpler to manufacture, less expensive and better suited to producing single-use ancillaries.

When the ancillary is thus heated in an autoclave for example, to try and "re-sterilise" it at a Ti temperature of 137° for example, the metal inserts irreversibly come away from the body and the ancillary can no longer be used. We can therefore be sure that a new, well-sterilised ancillary will have to be used for a future operation.

By making these ancillaries largely in plastic, the manufacturing process is greatly facilitated (an injection moulding process is now possible) and the cost of the material is reduced. It was thought until now that plastic was not a suitable material for manufacturing these ancillaries, both for reasons of hardness and because it was thought preferable to be able to reuse the ancillary. However, as the plastic used is hard enough, it will be suitable for removing bone and withstanding the pressures associated with the action of a blade on the bone. In addition, by producing the ancillary in plastic, there are greater capacities for manufacturing a single-use, so-called "disposable" ancillary.

As a result of an improvement to the invention, the hardness of the plastic is chosen close to the bone hardness, for example between 5 and 30% higher.

By producing the rasp or cutting unit in this material therefore, we make sure that the ancillary can only be used for a single operation since the material rapidly wears out during the operation to the extent that the ancillary has deteriorated too much by the end of the operation to be able to be reused for another operation.

As a result of an improvement to the invention, the plastic is chosen so that it deteriorates at or above a Ti temperature between 50° C. and 200° C., preferably between 70° C. and 150° C., specifically at or above a temperature equal to 137° C. We can then be sure that if the surgeon carries out sterilisation by autoclave, notably sterilisation at or below 137° C. to ensure that all the prions are fully removed, he will see his cutting unit or rasp deteriorating and will no longer be able to use them.

The initial sterilisation is actually carried out by exposure to γ or β rays. It can only be done once. A second exposure actually degrades the plastic due to the development of free radicals. The only way until now, therefore, of re-sterilising after initial use was to put the item through an autoclave. As a result of this improvement, this is no longer possible since the ancillary in the autoclave deteriorates and self-destructs. The ancillary can thus no longer be reused legally, although the surgeon can always reuse the ancillary without re-sterilising, but at is his own professional risk, of course.

According to a favourite production method, the plastic is a thermoplastic material, notably a polyvinyl, polyolefin, polyamide or similar material and it deteriorates in particular due to softening.

These materials are structurally not very solid. Nevertheless, they are perfectly well suited for use as a rasp or cutting unit for removing bone, which on the face of it may seem surprising, since one could expect that a rasp or a cutting unit would be produced in a material that has a certain hardness and a certain stress resistance. It transpires, however, that this rasp or cutting unit, which is made at least in part of a thermoplastic material, is perfectly well suited for use. In addition, since the thermoplastic material deteriorates due to softening at 137° C., and even at a temperature below 137° C., we can be certain that the surgeon will not be able to reuse these ancillaries. Finally, as they are largely plastic, they are inexpensive and can therefore be produced on a large scale and disposed of without involving very high running costs.

The aim of this invention is also a surgeon's kit for fitting prostheses, notably hip or knee prostheses, comprising a rasp according to the invention and other ancillaries also in plastic, or a kit comprising a cutting unit according to the invention and one or more other ancillaries also in plastic, the kit being vacuum packed or packed in a sterile atmosphere.

As a result of an improvement to the invention, the ancillary comprises at least one insert in an appreciably harder material than the plastic, metal for example, the insert being at least partly embedded in the plastic and in direct contact with the plastic.

When the plastic, for example, thus softens (as in the case of thermoplastic) or deteriorates due to decomposition (thermosetting plastic), contact with the insert is broken and the latter can notably break away from the body of the ancillary or assume a non-operational position and the ancillary becomes unusable.

As a result of an improvement to the invention, the ancillary comprises one part in a shape memory material harder than the plastic, the shape memory material taking an initial shape above a given Ti temperature, and a second shape below this given Ti temperature, the initial shape being such that when the temperature exceeds Ti and the material takes on this initial shape by itself, the ancillary is then at least partly destroyed.

Figure 1:
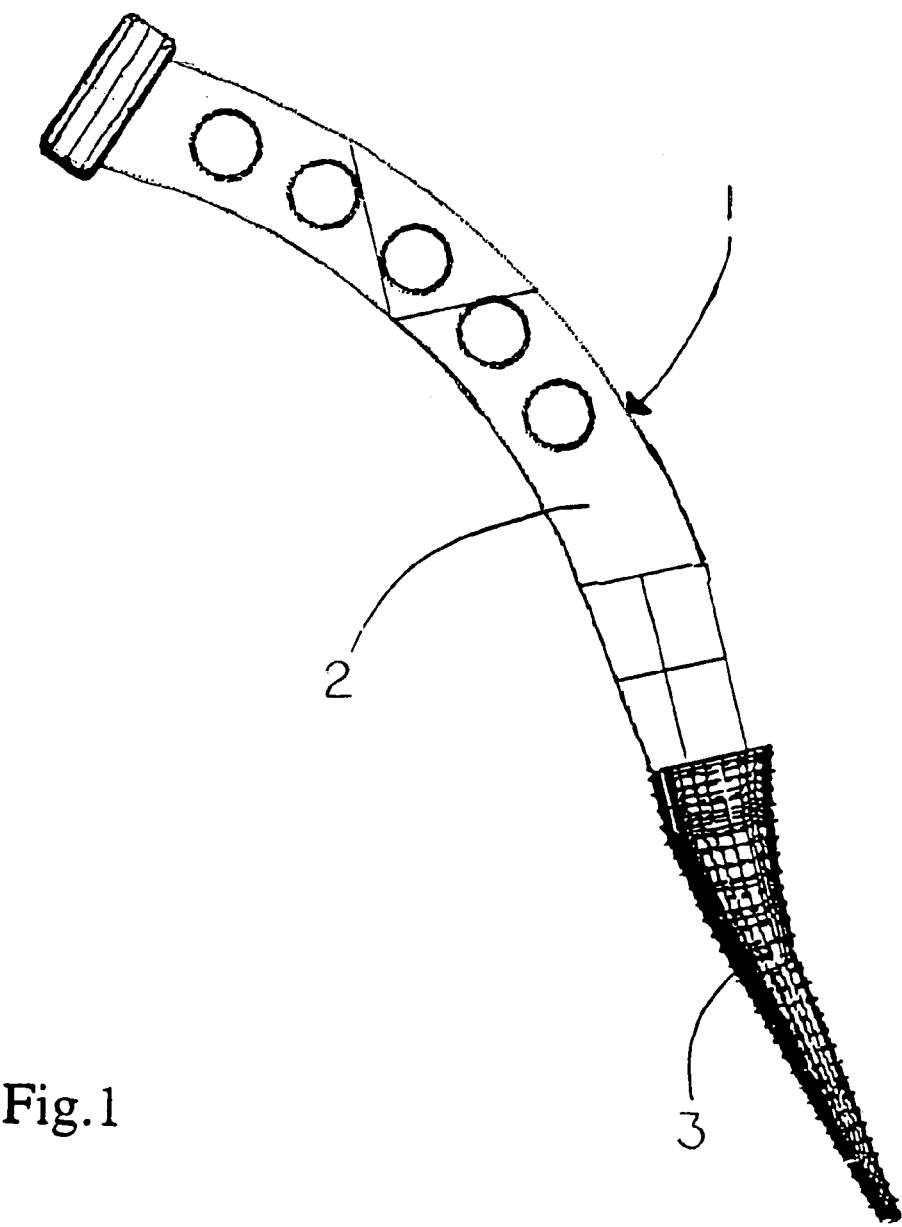
FIG. 1 shows a rasp according to the invention for cutting a bone to fit a hip prosthetic.

FIG. 1 shows a rasp 1 for a hip prosthesis. It consists of a curved, cylindrical grab handle 2 and of a part 3 of a rasp spiked with protrusions for rubbing the bone to reduce it to powder.

Rasp part 3 is locked at one end of handle 2 by a locking system.

Rasp part 3 is made of plastic, notably low or high-density polyethylene (LDPE, HDPE), polypropylene, polyacetal, PVC, etc.

LDPE softens at 104° C. and melts at 108-120° C., its Shore D hardness being 45-55.

The HDPE softens at 123-127° C. and melts at 125-135° C., its Shore D hardness being equal to 65-70.

PP softens at 149° C. and melts at 170° C., at a Shore D hardness of 80.

Handle 2 is made of plastic, for example HDPE.

According to another form of construction shown in the Figure, the protrusions of rasp part 3 are formed by inserts 4 in a harder material, notably metal, which protrude from the plastic, being largely embedded in it.

To form rasp 3, a cast is taken by pouring or injection into a mould, inserts 4 being positioned prior to injection in the position they are required to have in the final volume of plastic, then the plastic is poured into the mould and left to cool to produce the final rasp.

The inserts also increase the rasp's rigidity. When the rasp is placed in an autoclave for further sterilisation, the plastic softens above the Ti and the inserts come away from the plastic. The rasp can no longer be used. If the rasp has no inserts (the protrusions are made of plastic that is harder than the bone), the rasp is also unusable, the protrusions tending to disappear when the plastic softens.

According to another form of the invention, rasp 3 is formed by pouring or injecting the plastic, at least partly, and preferably completely, coating a rod 5 in a harder material, notably a shape memory metal. Before pouring the plastic, the rod is heated to a high temperature (above Te, which is lower than 137°) and assigned a given shape, bent back into a U for example, so that when rod 5 changes shape to take the given shape in question, it breaks its surrounding material, notably a plastic, which is softer, and the rasp is unusable.

Figure 2:
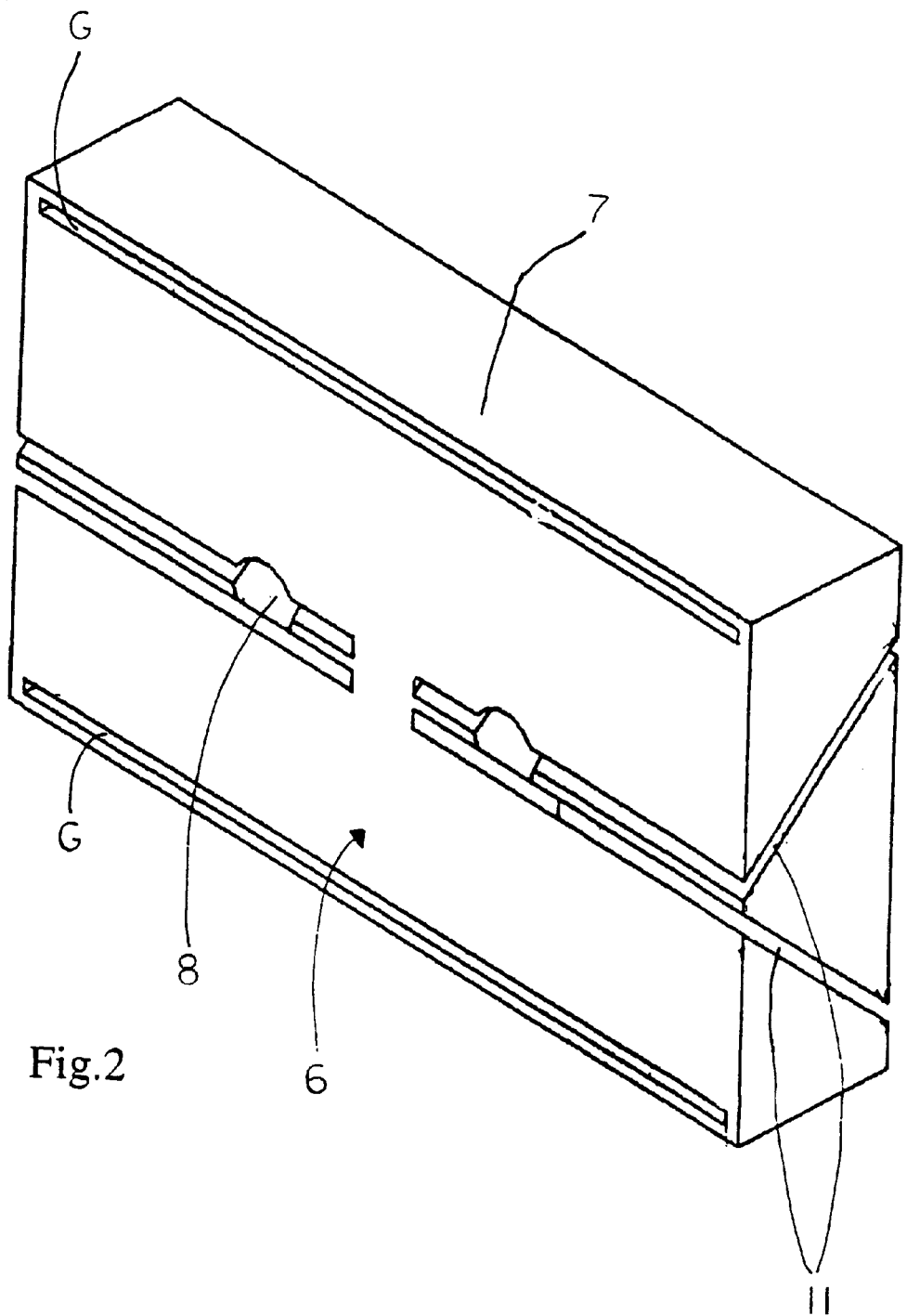
FIG. 2 shows a cutting unit for cutting a bone of the femur or tibia.

FIG. 2 shows a cutting unit 6 for a knee prosthesis. This unit 6 consists of a box-shaped body 7 drilled with two holes 8 for fixing by screw to the bone to be cut and comprises two horizontal slots 9 and two sloping slots 11, through which cutting blades can be inserted to resection bones for installing the prosthesis, slots 9 and/or 11 being chosen according to the angle of attack of the cut required.

The cutting unit is made of plastic, notably LDPE, HDPE, PP or similar.

Figure 4:
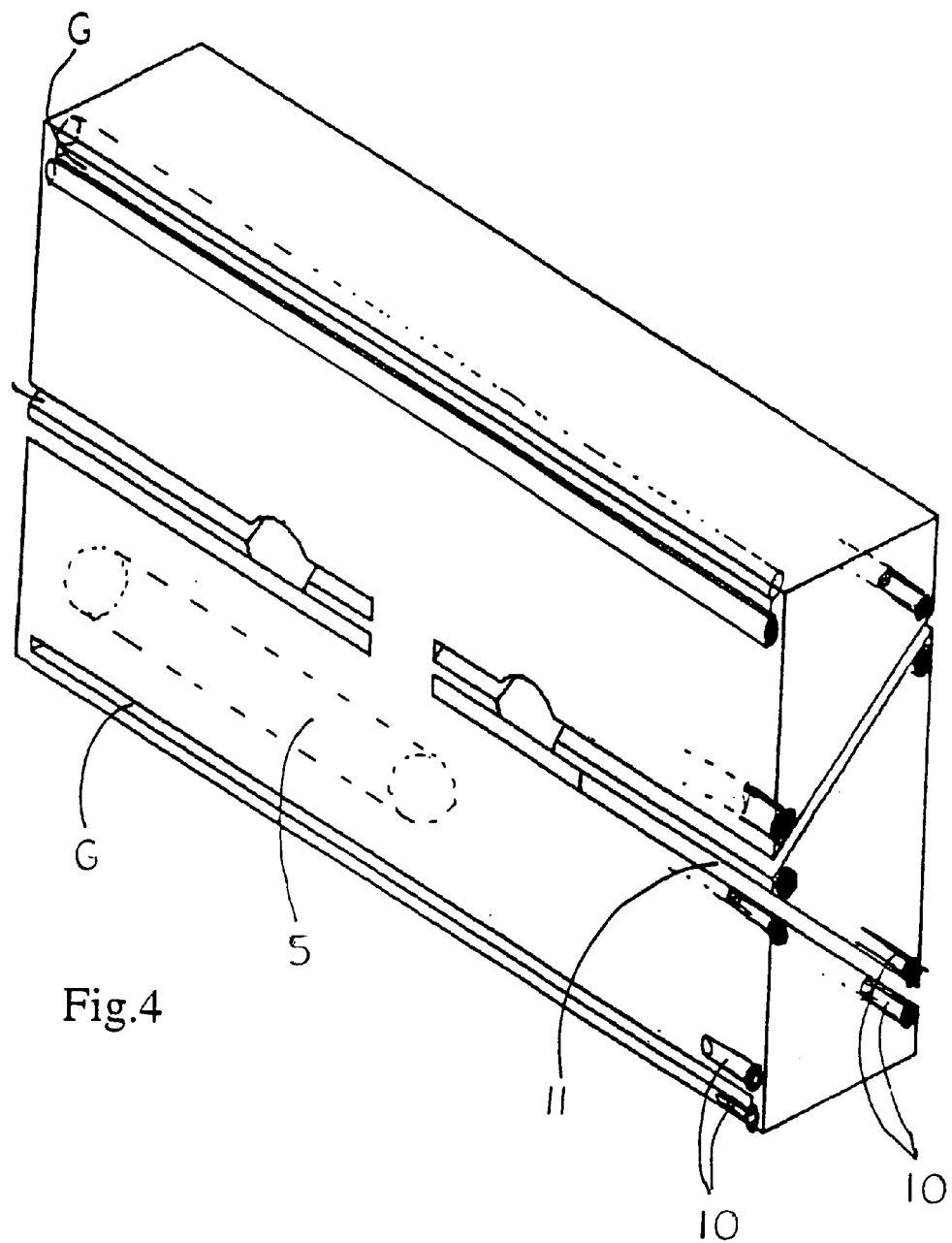
FIG. 4 shows an alternative to the unit in FIG. 2.
Figure 5:
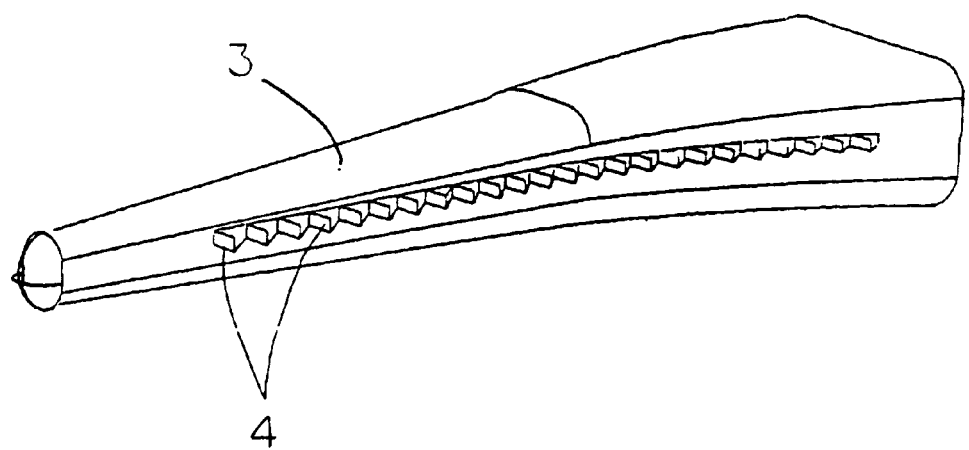
FIG. 5 shows an alternative to the rasp in FIG. 1.

It is formed by injection moulding. Metal inserts with or without shape memory and at least partly embedded in the plastic mass can be used in the same way as for the rasp described above. As can be seen in FIG. 4, metal inserts 10 in the form of flexes are arranged on both sides of the openings of slots 9 and 11 to support the blades inserted into the slots during their cutting action on the bone.

Figure 3:
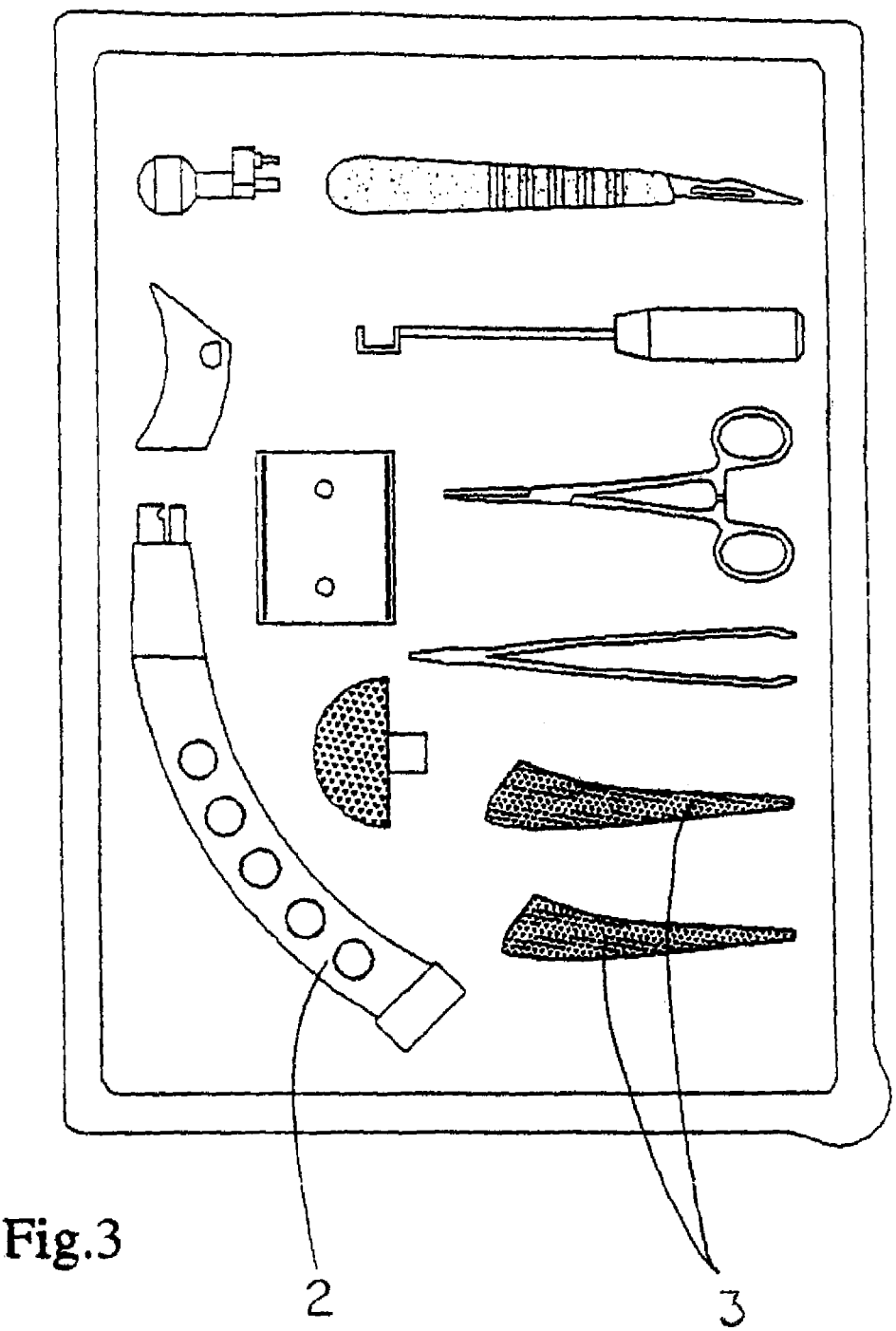
FIG. 3 shows a kit according to the invention.

FIG. 3 shows a tray vacuum-packed with a plastic film sealed at the edges of the tray. Several disposable ancillaries are packed in this tray, some or preferably all of which are partly or entirely made of one or more materials that deteriorate above a Ti temperature between 50° C. and 200° C., preferably between 70° C. and 150° C. and specifically at or above 137° C.

Bone hardness depends on the application, the patient and notably on his or her age. An appropriate plastic will be chosen according to the end use of each ancillary and to whether it is used, for example, to attack the (softer) spongy or (harder) cortical bone.

Figure 6:
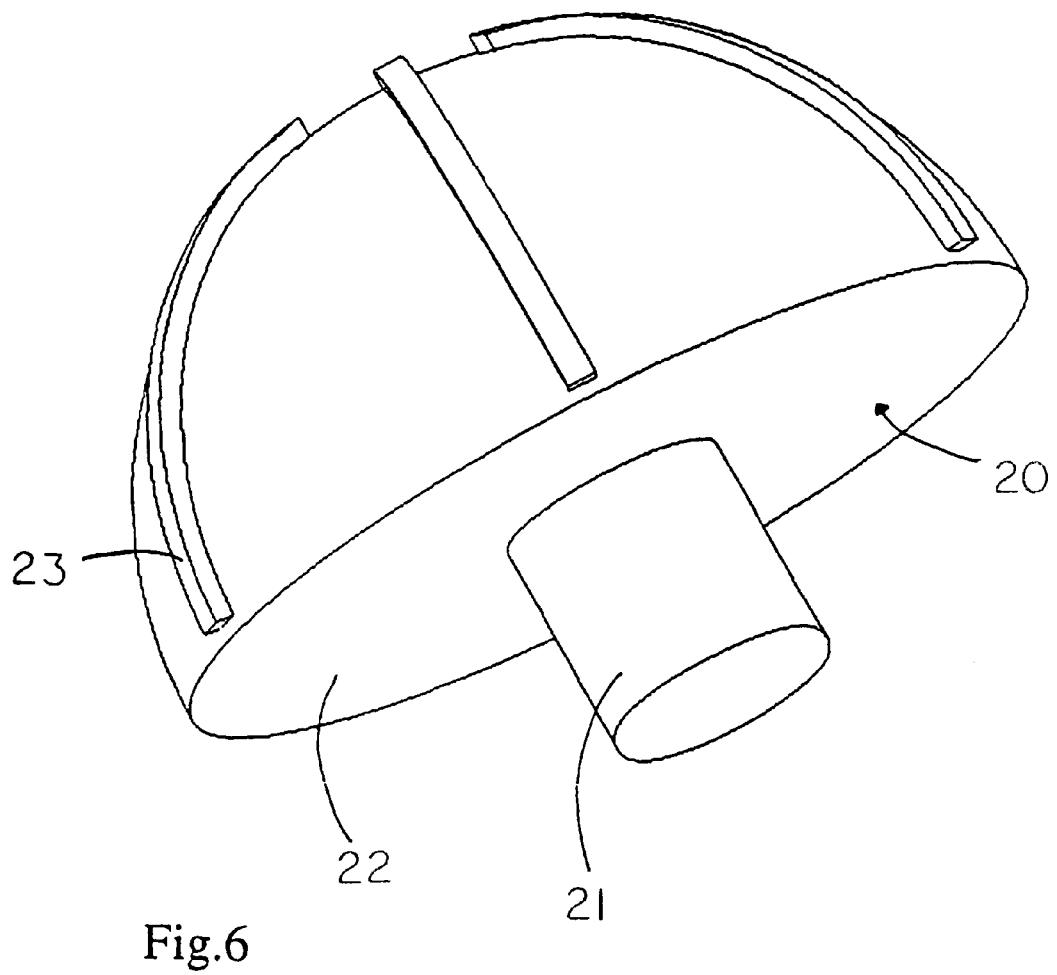
FIG. 6 shows an acetabulum drill according to the invention.

FIG. 6 shows a rasp for acetabulum or drill 20 with acetabulum.

Drill 20 consists of a rod 21 and a hemispherical head 22. Metal blades 23 are embedded in the plastic mass of head 22 and protrude from it as ribs for attacking the bone. Ribs 23 in plastic that is harder than the bone can also be formed in place of the blades by pouring into a suitable mould, that is, one with grooves corresponding to the ribs.

The invention claimed is:

1. A rasp for removing a part of a hip cortical bone from the hip cortical bone, comprising protrusions made of a plastic material which are to come into contact with the part of the hip cortical bone and to rasp it from the hip cortical bone, said plastic material being hard enough for the removal of hip cortical bone, and wherein said rasp wears out after a single use and when said rasp is put into an autoclave at at least 137° C., said rasp deteriorates itself and cannot be used anymore.

2. The rasp as recited in claim 1, wherein said rasp also comprises at least one insert of a material which is harder than hip cortical bone, said at least one insert being at least partly embedded in said plastic material.

3. The rasp as defined in claim 2, wherein said at least one insert is fully embedded in said plastic material.

4. The rasp as defined in claim 3, wherein said at least one insert is a metal.

5. The rasp as defined in claim 2, wherein said at least one insert is a metal.

6. The rasp as defined in claim 1, wherein said rasp comprises a part of a shape memory material harder than said plastic material.

7. The rasp as defined in claim 1, wherein said plastic material is exposed to β or γ rays.

8. A method for manufacturing a rasp for removing a part of a hip cortical bone from the hip cortical bone, comprising the steps of:

providing a body having the shape of a rasp and comprising protrusions made of a plastic material which are to come into contact with the part of the bone and to rasp it from the bone when said rasp is used to remove the part of the bone; and exposing said plastic material β or γ rays, so that after this exposition, said plastic material is hard enough to remove the part of the hip cortical bone from the hip cortical bone when said rasp is used and wears out after a single use, and when said rasp is put into an autoclave at at least 137° C., said rasp deteriorates itself and cannot be used anymore.

9. The method of claim 8, further comprising the step of embedding at least one insert of a material harder than hip cortical bone in the plastic material.

10. The method of claim 9, wherein the at least one insert is fully embedded in the plastic material.

* * * * *